(12) United States Patent
Harrison

(10) Patent No.: US 10,639,444 B2
(45) Date of Patent: May 5, 2020

(54) FACIAL MASK WITH INTERNAL INTERMEDIATE MAXILLA SUPPORT FOR USE WITH VENTILATION AND POSITIVE AIR PRESSURE SYSTEMS

(71) Applicant: Donald Harrison, Park City, UT (US)

(72) Inventor: Donald Harrison, Park City, UT (US)

(73) Assignee: BREAS MEDICAL, INC., North Billerica, MA (US)

( * ) Notice: Subject to any disclaimer, the term of this patent is extended or adjusted under 35 U.S.C. 154(b) by 984 days.

(21) Appl. No.: 15/085,076

(22) Filed: Mar. 30, 2016

(65) Prior Publication Data

US 2016/0287828 A1 Oct. 6, 2016

Related U.S. Application Data

(60) Provisional application No. 62/140,690, filed on Mar. 31, 2015.

(51) Int. Cl.
*A61M 16/06* (2006.01)
*A61M 16/08* (2006.01)

(52) U.S. Cl.
CPC .... *A61M 16/0616* (2014.02); *A61M 16/0683* (2013.01); *A61M 16/0816* (2013.01)

(58) Field of Classification Search
CPC .... A61M 16/00; A61M 16/06; A61M 16/021; A61M 16/022; A61M 16/024; A61M 16/026; A61M 16/0605; A61M 16/0616; A61M 16/1045; A61M 16/105; A61M 16/0683; A61M 16/0816; A61M 16/0093; A61M 16/0461; A61M 16/0666; A61M 16/0672; A61M 2016/0661; A61M 2205/75; A62B 18/02; A62B 18/025
See application file for complete search history.

(56) References Cited

U.S. PATENT DOCUMENTS

| 2,578,621 | A | * | 12/1951 | Yant | A62B 18/025 |
| | | | | | 128/206.24 |
| 3,583,396 | A | * | 6/1971 | Landis | A61H 15/0092 |
| | | | | | 601/125 |
| 4,132,230 | A | * | 1/1979 | Ladd | A61F 5/3784 |
| | | | | | 128/874 |
| 5,025,805 | A | * | 6/1991 | Nutter | A61M 16/0666 |
| | | | | | 128/207.18 |
| 5,724,965 | A | | 3/1998 | Handke et al. | |
| 6,082,360 | A | * | 7/2000 | Rudolph | A61M 16/06 |
| | | | | | 128/206.24 |
| 6,123,071 | A | | 9/2000 | Berthon-Jones | |
| 6,629,531 | B2 | | 10/2003 | Gleason | |
| 7,210,481 | B1 | | 5/2007 | Lovell et al. | |
| 7,455,063 | B2 | | 11/2008 | Geiselhart | |

(Continued)

FOREIGN PATENT DOCUMENTS

FR 3018194 A1 * 9/2015 ............ A61M 11/06

*Primary Examiner* — Justine R Yu
*Assistant Examiner* — Jacqueline M Pinderski
(74) *Attorney, Agent, or Firm* — Yi Liu

(57) ABSTRACT

The present disclosure relates to a facial mask system having an internal intermediate maxilla support structure for providing increased support and decreased occurrence of points having increased pressure concentration on a user's face, where the maxilla support system provides a comfortable, uniform sealing force around the breathing passages of a user.

19 Claims, 4 Drawing Sheets

(56) References Cited

U.S. PATENT DOCUMENTS

| | | |
|---|---|---|
| 7,958,893 B2 | 6/2011 | Lithgow |
| 7,997,267 B2 | 8/2011 | Ging |
| 8,371,302 B2 | 2/2013 | Ging et al. |
| 8,602,029 B2 | 12/2013 | Gradon et al. |
| 8,813,749 B2 | 8/2014 | Hernandez et al. |
| 10,143,817 B2 * | 12/2018 | Chodkowski ......... A61M 16/06 128/206.24 |
| 2003/0168063 A1 | 9/2003 | Gambone |
| 2004/0226563 A1 * | 11/2004 | Xu ......................... A62B 18/02 128/206.21 |
| 2006/0118117 A1 * | 6/2006 | Berthon-Jones ...... A61M 16/06 128/206.21 |
| 2007/0215161 A1 | 9/2007 | Frater |
| 2009/0139525 A1 | 6/2009 | Schirm |
| 2010/0065058 A1 | 3/2010 | Ungar |
| 2011/0088699 A1 | 4/2011 | Skipper |
| 2012/0222680 A1 | 9/2012 | Eves |
| 2012/0305001 A1 * | 12/2012 | Tatkov .................. A61M 16/06 128/205.25 |
| 2014/0150799 A1 | 6/2014 | Daly |
| 2014/0166018 A1 | 6/2014 | Dravitzki |
| 2014/0366886 A1 * | 12/2014 | Chodkowski ......... A61M 16/06 128/206.24 |
| 2015/0075531 A1 | 3/2015 | Gong |

\* cited by examiner

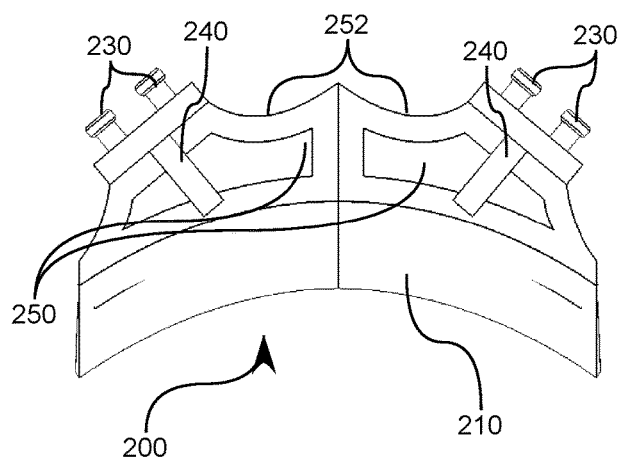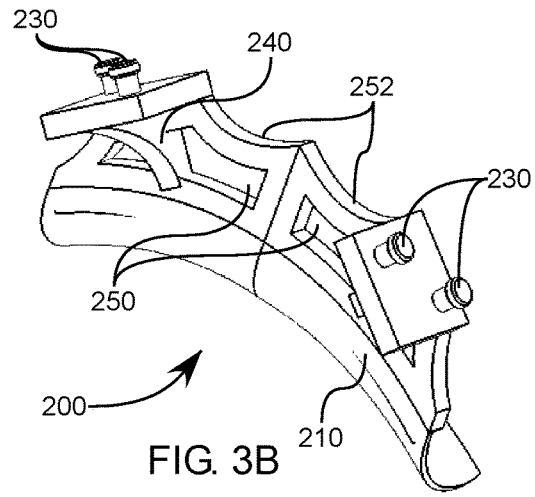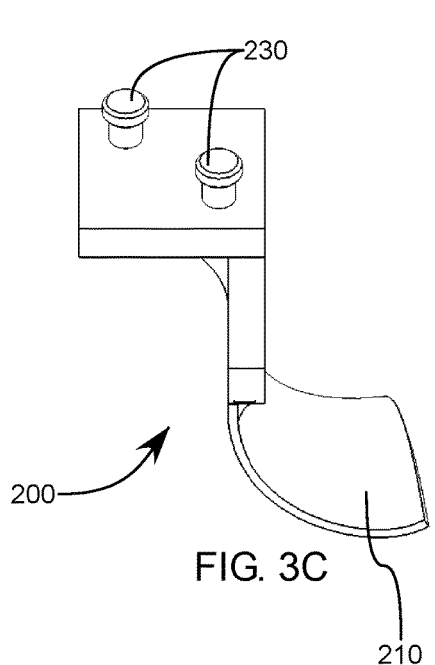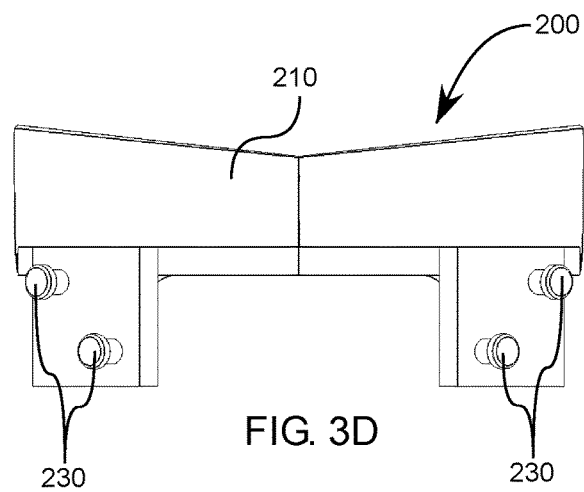
FIG. 3A
FIG. 3B
FIG. 3C
FIG. 3D

FACIAL MASK WITH INTERNAL INTERMEDIATE MAXILLA SUPPORT FOR USE WITH VENTILATION AND POSITIVE AIR PRESSURE SYSTEMS

PRIORITY CLAIM

Priority is claimed to U.S. Provisional Patent Application Ser. No. 62/140,690 filed Mar. 31, 2015, which is hereby incorporated by reference in its entirety.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to medical devices, and, more particularly to masks and headgear portions of air delivery devices that assist with the delivery of gas to the breathing airways of users. These mask and headgear systems and devices can be used with positive airway pressure (PAP) such as continuous positive airway pressure devices (CPAP), automatic positive airway pressure devices (APAP), variable positive airway pressure devices (VPAP), and bi-level positive airway pressure devices (BPAP).

2. Description of the Prior Art

Previous masks have been bulky, heavy, and/or difficult to secure over a user's breathing airways. Additionally, the pressure on and around the face required to maintain a bulky nasal mask system in place can be uncomfortable. Previous systems which cover both nose and mouth are often overly bulky or otherwise cumbersome to wear.

The present invention seeks to address these concerns by providing a mask system having an internal intermediate maxilla support that provides increased support and decreases the occurrence of points having increased pressure concentrations about the user's face.

SUMMARY OF THE INVENTION

In one embodiment a mask is provided having a shell, the shell having an internal supporting structure that provides support to and provides rigidity to the shell. The shell provides a recess into which a user can insert the user's nose, the user's mouth, or both in order to breathe air provided to the interior, the mask being configured to sealingly adapt over and around a user's breathing airways. The mask can be configured to connect to a headgear or other strapping assembly so as to provide a sealing force between the mask and the user's face. An exterior circumference of the mask can be provided with a sealing membrane provided about the outer rim of the shell in the form of a membrane, conforming material, or other soft resilient material so as to allow for a comfortable fit and seal between the edge of the mask and the user's face. The frame can further include a structural grid work or frame configured to provide additional strength and rigidity to the shell and in particular when transferring the sealing force between the shell and an area around the nose and mouth of the user, and between the intermediate maxilla support and the maxilla of the patient provided by the headgear.

The intermediate maxilla support can be configured to be received within the recess of the shell, the intermediate maxilla support being further configured to provide a supporting force to the shell from a portion of the user's face being defined by a portion of the maxilla between the nose and lips of the user.

The intermediate maxilla support can further be configured to be removable so as to better suit the varying preferences between potential users. In order to be removable, the intermediate maxilla support can be coupled to an interior surface of the shell or frame supporting the shell, the coupling can be provided using a plurality of tabs being provided on the intermediate maxilla support, the plurality of tabs being configured to mate to and interferingly engage with a plurality of receivers being provided on the interior surface of the shell. In will be appreciated that alternative attachment or connection components or means contemplated herein, but not shown, can include a detachable adhesive, hook and loop fasteners, magnetic, latching mechanisms, various press-fit mechanisms, or other suitable placement mechanisms which can suitably retain positioning under the load, as the majority of the force transferred therethrough is a compressive force.

The intermediate maxilla support can further include a support surface which contacts the portion of the maxilla between the nose and lips of the user, wherein a malleable conforming material can be provided on the support surface between the intermediate maxilla support and the portion of the maxilla between the nose and lips of the user.

It will be appreciated that the location of the intermediate maxilla support can effectively divide the recess within the shell into two portions, one in direct communication with the nares and the other in direct communication with the mouth. This separation can cause unwanted flow complications. In order to overcome these potential complications the intermediate maxilla support can further be provided with a plurality of air channels provided through the intermediate maxilla support between a mouth portion and nasal portion of the recess.

The intermediate maxilla support can be provided with increased strength by utilizing a structural grid work in the form of a cross grid or latticework in the intermediate maxilla support so as to maintain give a certain degree of shape retention and support the applied forces between the attachment means to the internal support structure of the shell and the conforming material or membrane which rests on the maxilla between the mouth and nose of the user while allowing air to travel between the divided recesses within the shell.

The can also be formed using a shape retaining and customizable polymer. Additionally, the conforming material can be provided as a silicone being overmolded onto the intermediate maxilla support.

These and other embodiments are described in more detail herein.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 3A-D illustrate top, perspective, side and front views respectively of an intermediate maxilla support for use with the mask system of FIGS. 1-2;

DETAILED DESCRIPTION OF THE PREFERRED EMBODIMENT

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below can be combined with one another in any suitable manner and can be adapted and applied to other PAP apparatuses, systems, and methods, including, but not limited to, APAP, VPAP, and BPAP apparatuses, systems, and methods.

The present application seeks to provide a solution to the aforementioned problems by creating an adjustable, comfortable, mask assembly system that has interchangeable components, is light-weight, and provides a uniform sealing around an area surrounding a user's nasal passages and mouth which is enabled by a unique internal intermediate maxilla support which can be optionally provided to a mask system.

Figure 1A:
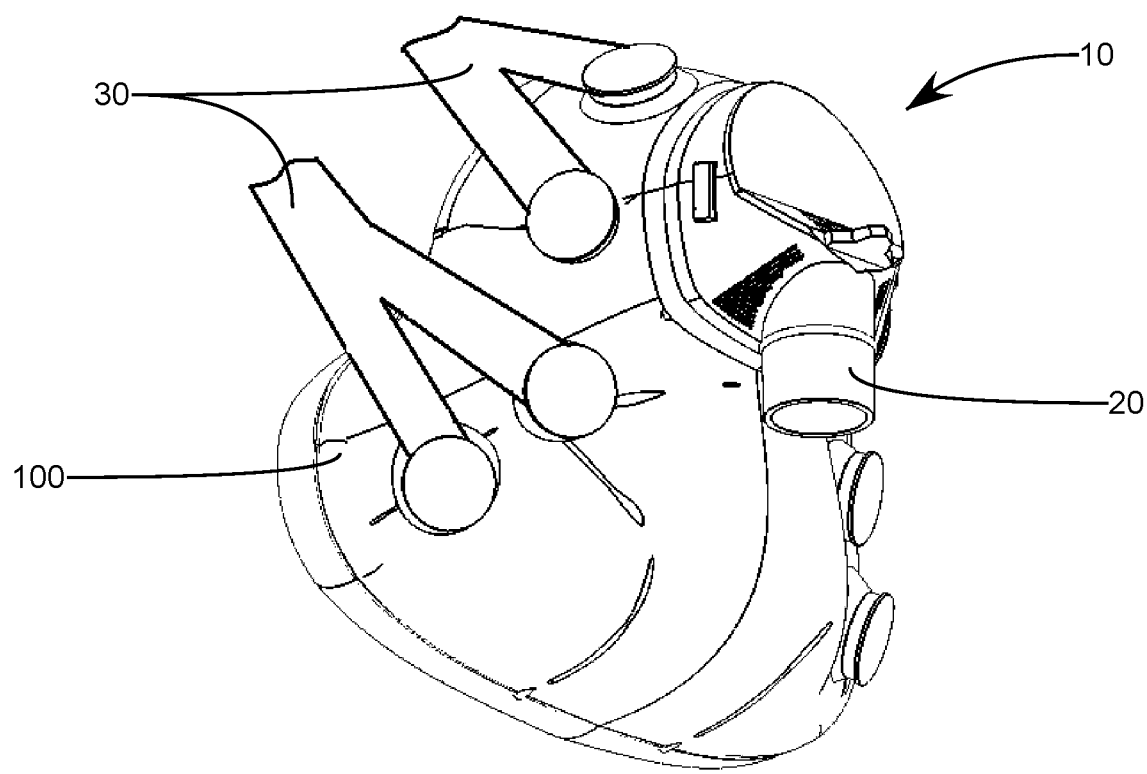
FIGS. 1A-B illustrate front and rear perspective partially assembled views of a mask system and intermediate maxilla support in accordance with one embodiment of the present invention.
Figure 1B:
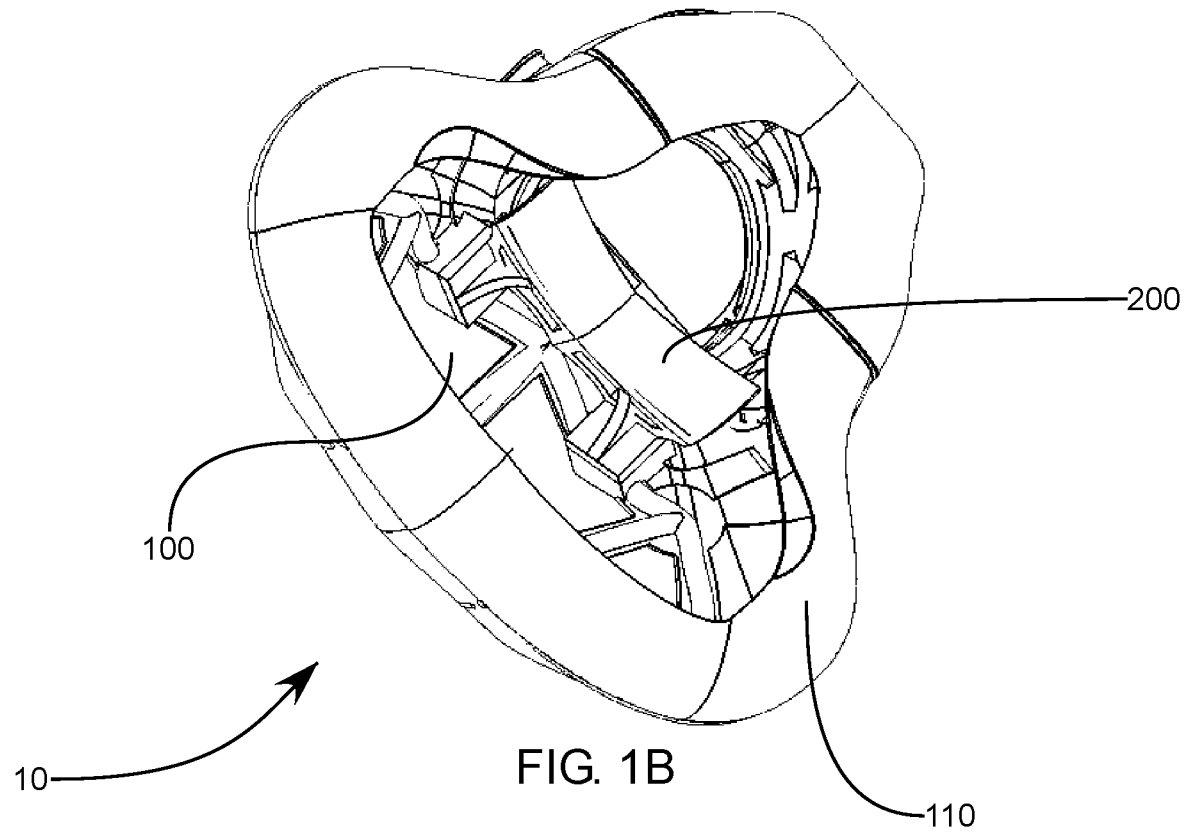
Figure 2:
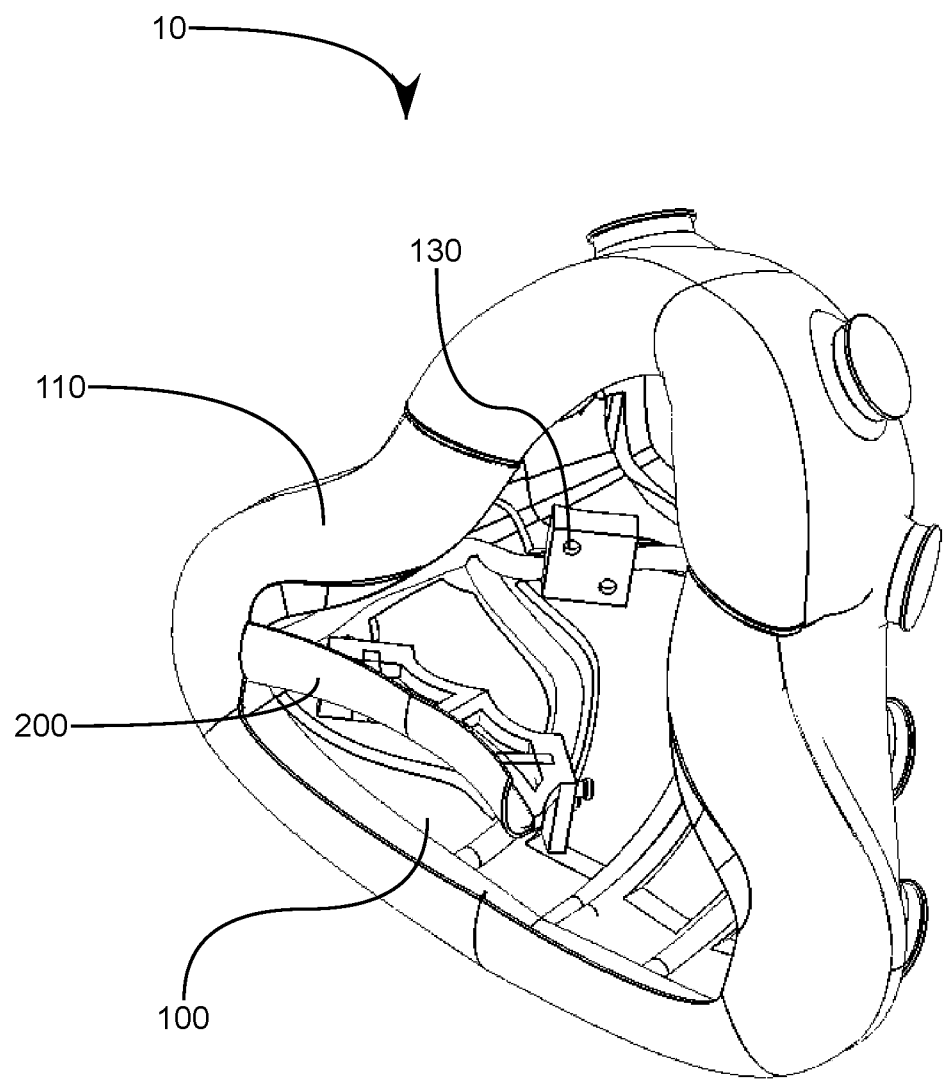
FIG. 2 illustrates a rear perspective exploded view of a mask system and intermediate maxilla support in accordance with one embodiment of the present invention.

FIGS. 1-2 illustrate a mask system 10, the mask system 10 having a shell 100 connected to a positive pressure air supply source (not shown). The positive pressure air supply can be provided via various methods, the method depicted here includes an inlet adapter 20 which can be fluidly connected to a CPAP pump, blower, etc. (not shown) which can thus be provided with pressurized air flow. In this manner positive air pressure or flow can be supplied into the mask assembly, into the shell, wherein a user can breathe the positive pressure air supply by placing the shell 100 over their mouth and nose with their mouth and nose entering into a recess formed by the shell.

It will be appreciated that a headgear or strap assembly 30 can be used to exert a sealing force between the shell and the user's face. The shell can be provided with a sealing membrane or conforming material 110 which can operate to provide a comfortable seal around the user's mouth and nose so as to maintain the positive air pressure within the recess. In previous mask systems, and particularly in those covering both the mouth and the nose, the sealing membrane or conforming material can in certain cases create pressure points due to the varying contours of the user's face. In certain instances the sealing force applied by the strap or headgear assembly 30 can be increased or adjusted so as to apply a proper sealing force and adjusts such pressure points so as to maximize comfort. However, it has been recognized, and is part of the present invention, that an under nose support 200 can be provided which attaches to an interior surface of the shell and can direct or adjust the sealing force into a portion of the maxilla of the patient and thus better disperse the placement and sealing force provided by the provided headgear assembly 30, namely by directing this force into a portion of the maxilla between the mouth and nose of the patient.

FIGS. 1-2 illustrate one embodiment of an intermediate maxilla support 200, and FIGS. 3A-D illustrate various views of an alternative embodiment of an intermediate maxilla support 200. The main difference being the orientation and design of a support surface 210 which rests upon the skin of the patient between the mouth and the nose, directing a portion of the sealing force into the maxilla of the patient. FIGS. 1-2 illustrate a semi rigid and contoured support surface, while FIGS. 3A-D illustrate a flexible or curved membrane support surface. The support surface 210 can be provided as a soft silicone, or it can be provided having a rigid construction and subsequently overmolded with a flexible or soft conforming material. In some embodiments a soft support surface can encapsulate an air pocket or other conforming material so as to provide a soft interface which can be easily cleaned or otherwise sanitized.

FIGS. 3A-D also illustrates how the intermediate maxilla support 200 can be provided with a grid or lattice type support structure 240 which is provided as a plurality of multiaxial beams or trusses construction so as to maintain a lightweight profile for maintaining the comfort and ease of use for the patient. It will also be appreciated that a solid intermediate maxilla support could result in a separation of the recess of the shell into a nasal portion and a mouth portion. In such cases a pressure differential could be formed across the two portions which could result in unwanted airflow or pressure characteristics. In order to maintain proper airflow and pressure, a plurality of air channels 250 can be provided through the intermediate maxilla support. It will also be appreciated that the intermediate maxilla support can be configured so as to not extend the entire width of the mask, having cutouts 252 about a perimeter edge, so as to allow air flow around the sides of the intermediate maxilla support between the edges of the intermediate maxilla support and the shell of the mask.

As discussed briefly above, the intermediate maxilla support 200 can be removably inserted into the shell 100. The coupling required in order to maintain the intermediate maxilla support in proper orientation and placement can be provided by a coupling interface, shown herein by a plurality of protrusions 230 and corresponding receivers 130. The protrusions 230 can be provided with flared or mushroomed ends which interferingly engage the receivers 130 when pressed therein. The fit between the two can be provided as a snap fit, an interference fit, or a friction fit, so as to facilitate removal when or if desired by the patient. It will be appreciated that the mask has sufficient internal structure so as to be functional without the use of the intermediate maxilla support 200.

The grid work also allows for the intermediate maxilla support to be customized to a certain degree. As discussed above, the intermediate maxilla support can be formed of a shape retaining plastic. Shape retaining plastic can be provided in several forms and of several different suitable materials. In the present embodiments the shape retaining plastic can be configured to allow a certain degree of manipulation by the patient so as to conform the plastic to specific contours of features of the patient's face. In other embodiments, a malleable material can be provided or overmolded onto a semi-rigid intermediate maxilla support, wherein the malleable material can be customized as necessary. In each of the embodiments, the intermediate maxilla support can be provided in various initial sizes prior to customization to reduce the necessary amount of customization for each patient.

Figure 4:
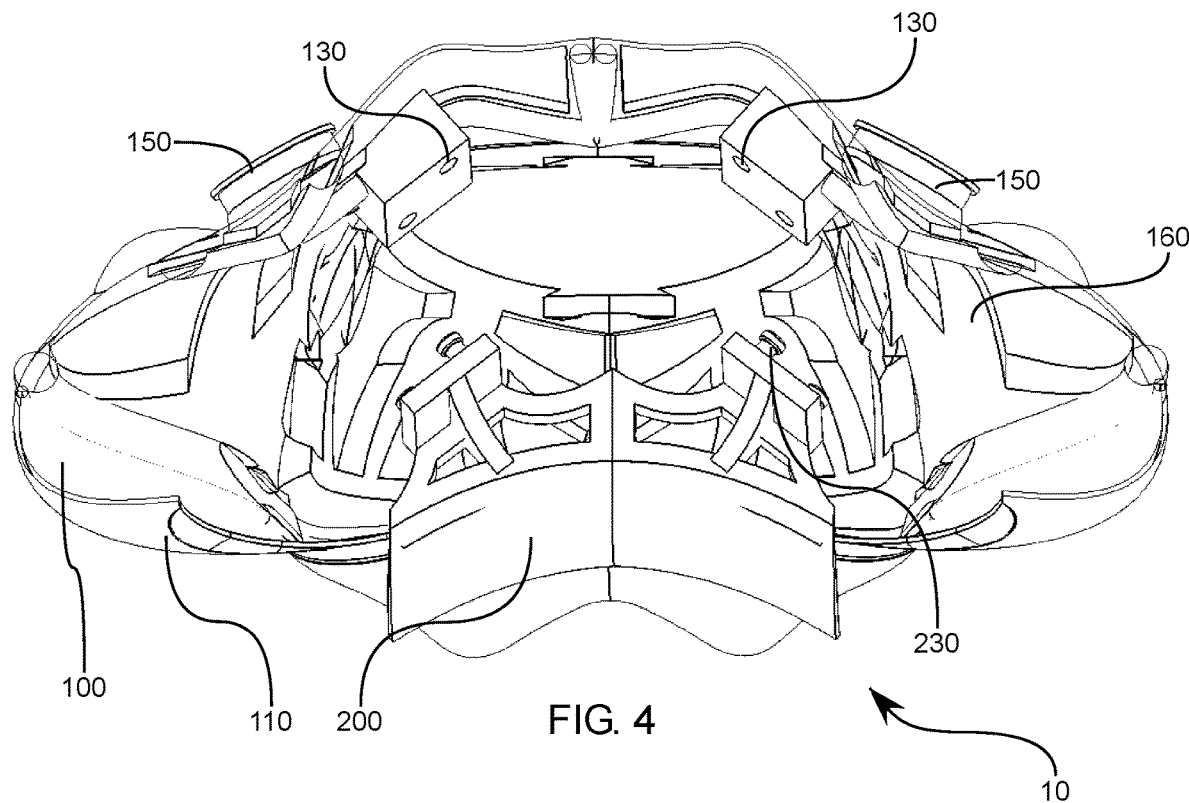
FIG. 4 illustrates a perspective cross-sectional view of the mask system in accordance with FIGS. 1-2 showing the intermediate maxilla support being partially separated from within the mas.
Figure 5:
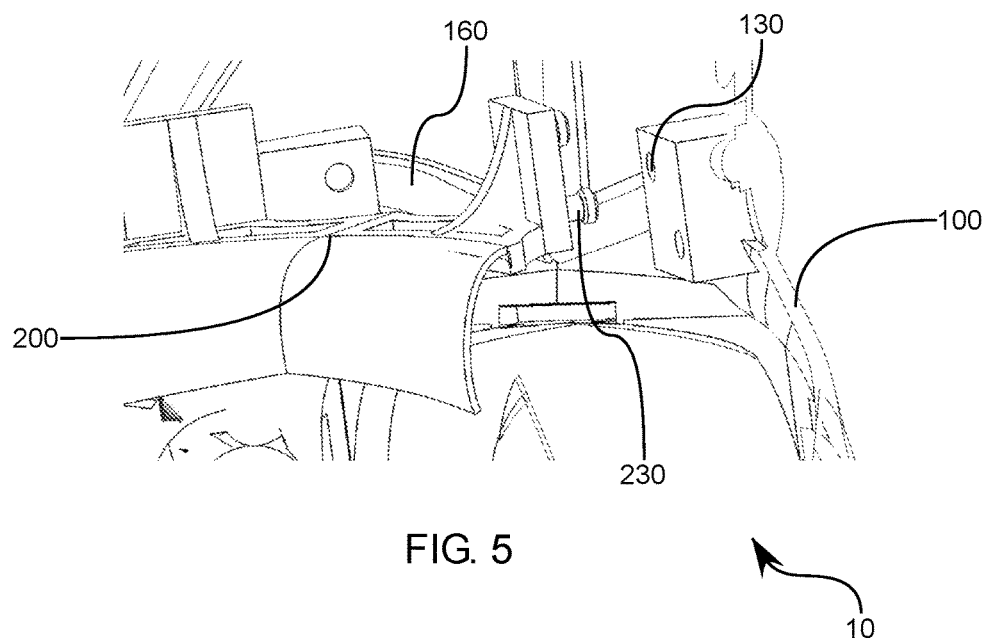
FIG. 5 illustrates a partial cross-sectional view of the intermediate maxilla support being separated from an interior surface of the mask.

FIGS. 4-5 illustrate the receivers 130 and the protrusions 230 in both connected and separated configurations. It will be further appreciated that the receivers 130 and the protrusions 230 can be replaced with various alternative fastening means, not shown, but which can include hook and loop fastening systems, reusable adhesive strips, suction means, magnetic fastening means, latches, press or other interference fits, etc. In the embodiments shown, the protrusions 230 can have flared or mushroomed distal ends which correspond to a flared or increased interior diameter of the receivers about a proximal, or most interior end of the receivers 130. In this manner the flexible material of both the mask, and receivers, as well as the protrusions 230 can deform slightly upon insertion and thus provide a stable interference fit between the mask and the intermediate maxilla support 200.

FIGS. 4-5 also illustrate how the shell can be provided with an internal lattice or support system in the form of a structural grid work or frame 160 which can allow for additional material removal within the shell and thus provide for lighter and stronger mask. The mask can also be provided with a strap or headgear interface 150 which transfers the force applied by the headgear, 30 as shown in FIG. 1A, and converts tension from the straps into a sealing force between the mask frame and the user's face.

The sealing membrane 110 can be provided with a substantially thin and flexible membrane material which can be provided with additional rigidity or is allowed to maintain a concave aperture into which the user's mouth can fit by means of an internal lattice work. For example, a structural grid work or frame 160 can be provided to form a supporting structure for a thin membrane or shell 100 that extends to cover the gaps between each of the structural components forming the frame 160.

It will be appreciated that various optional features including CO2 vent holes or other exhaust ports or apertures can be provided to the mask as deemed necessary. It will be appreciated that anti-asphyxia valve or ports can further be provided about the mask, or additionally a positive air pressure adapter. It will be appreciated that these features can be located on virtually any component of the mask assembly 10.

The sealing membrane 110 can be configured to extend inwardly from the outer edge or circumference of the shell 100 and me formed of a malleable material which conforms to the surfaces of the users face which are contained within the mask. The sealing membrane 110 can then receive the sealing force applied to the mask system 10 by the headgear strap assembly 30, wherein the sealing membrane deforms appropriately around the facial contours of the user so as to provide a seal between the interior of the mask system 10 and the user's face. It will be further appreciated that a plurality of these sealing membranes can be provided and arranged in echelon and extending from various points from the exterior of the rim and various points from the interior of the rim so as to provide a desired rigidity or conformation to the user's face.

It will be appreciated that individual users can have different sized noses and faces, thus in some aspects of the present invention the mask 100 can be provided in a plurality of scaled sizes appropriate for a specific user. It will be appreciated that various sizes and shaped mask systems can be provided so as to better fit the user and customize the mask system 10 based on the user's preference.

The above embodiments can be formed of various materials include silicone materials, plastics, and the like. Furthermore, the durometer of each of the materials can be varied. For example, the durometer of the outer shell can be more pliable compared to the internal intermediate maxilla support. Alternatively, the thicknesses of the internal intermediate maxilla support can vary to provide the necessary mechanical coupling of a force being applied to the attachment means.

The above description is merely illustrative. Having thus described several aspects of at least one embodiment of this invention including the preferred embodiments, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only. Additionally, any features described with respect to any one particular embodiment are not intended to be exclusive, but are applicable to any other embodiment as appropriate and with any necessary minor modifications thereto.

I claim:

1. A positive airway supply system comprising:
    a positive air pressure adapter being configured to connect to a positive air pressure source;
    a mask comprising:
        a shell forming a recess, wherein the recess is configured to receive air from the adapter; and
        an outer rim adapted to seal around the mouth and nose of a user; and
        an intermediate maxilla support configured to be received within the recess of the mask, wherein the intermediate maxilla support comprises a plurality of air channels through the intermediate maxilla support; and
        wherein the intermediate maxilla support is formed of a structural grid work in the form of a cross grid or latticework.

2. The positive airway supply system of claim 1, wherein the intermediate maxilla support is removable.

3. The positive airway supply system of claim 1, wherein the intermediate maxilla support comprises:
    a support surface configured to interact with the portion of the maxilla between the nose and lips of the user; and
    a malleable conforming material on the support surface.

4. The positive airway supply system of claim 3, wherein the malleable conforming material is silicone.

5. The positive airway supply system of claim 1, wherein the intermediate maxilla support is formed of a shape retaining polymer.

6. The positive airway supply system of claim 1, wherein the intermediate maxilla support is coupled to an interior surface of the shell.

7. The positive airway supply system of claim 6, wherein the shell comprises a structural grid work.

8. The positive airway supply system of claim 6, wherein the intermediate maxilla support comprises a plurality of tabs configured to mate to a plurality of receivers on an interior surface of the shell.

9. The positive airway supply system of claim 1, wherein the mask comprises a frame.

10. The positive airway supply system of claim 9, wherein the intermediate maxilla support is attached directly to the frame.

11. The positive airway supply system of claim 1, wherein the mask comprises a sealing membrane about the outer rim of the shell.

12. A positive airway supply system comprising:
a mask comprising:
a shell forming a recess, wherein the recess is configured to receive air from the positive air pressure source and the shell comprises
an outer rim;
a support frame about which the shell is formed; and
an intermediate maxilla support configured to be received within the recess of the shell and attached to the support frame,
wherein the intermediate maxilla support comprises a support surface configured to interact with the portion of the maxilla between the nose and lips of a user and a malleable conforming material on the support surface;
wherein the intermediate maxilla support is formed of a structural grid work in the form of a cross grid or latticework; and
a headgear or strap assembly attached to an outer surface of the shell.

13. The positive airway supply system of claim 12, wherein the intermediate maxilla support is removable.

14. The positive airway supply system of claim 12, wherein the intermediate maxilla support comprises a plurality of air channels through the intermediate maxilla support.

15. The positive airway supply system of claim 12, wherein the intermediate maxilla support is formed of a shape retaining polymer.

16. The positive airway supply system of claim 12, wherein the intermediate maxilla support is coupled to an interior surface of the shell.

17. The positive airway supply system of claim 12, wherein the malleable conforming material is silicone.

18. The positive airway supply system of claim 12, comprising a sealing membrane provided about the outer rim of the shell.

19. A positive airway supply system comprising:
a mask comprising:
a shell forming a recess, wherein the recess is configured to receive air from a positive air pressure source and the shell comprises
an outer rim;
a frame supporting the shell;
an intermediate maxilla support configured to be received within the recess of the shell, the intermediate maxilla support comprising:
a support surface;
a malleable conforming material on the support surface;
a plurality of air channels through the intermediate maxilla support;
a plurality of attachment components;
a plurality of complementary attachment components on an interior surface of the shell, wherein the plurality of attachment components are configured to mate to the plurality of complementary attachment components;
a sealing membrane about the outer rim of the shell;
a headgear or strap assembly; and
wherein the intermediate maxilla support is formed of a structural grid work in the form of a cross grid or latticework.

* * * * *